(12) United States Patent
Duan et al.

(10) Patent No.: US 10,527,439 B2
(45) Date of Patent: Jan. 7, 2020

(54) NAVIGATION SYSTEM BASED ON AIR POLLUTION EXPOSURE PROFILING

(71) Applicant: International Business Machines Corporation, Armonk, NY (US)

(72) Inventors: Ning Duan, Beijing (CN); Peng Ji, Nanjing (CN); Zhi Hu Wang, Beijing (CN); Guotao Zhao, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 339 days.

(21) Appl. No.: 15/397,962

(22) Filed: Jan. 4, 2017

(65) Prior Publication Data

US 2018/0188050 A1     Jul. 5, 2018

(51) Int. Cl.
| | |
|---|---|
| *G01C 21/34* | (2006.01) |
| *G08G 1/0968* | (2006.01) |
| *G08G 1/01* | (2006.01) |
| *G01N 33/00* | (2006.01) |

(52) U.S. Cl.
CPC ......... *G01C 21/3461* (2013.01); *G08G 1/012* (2013.01); *G08G 1/0112* (2013.01); *G08G 1/0116* (2013.01); *G08G 1/0129* (2013.01); *G08G 1/0141* (2013.01); *G08G 1/096811* (2013.01); *G08G 1/096838* (2013.01); *G01N 33/0075* (2013.01)

(58) Field of Classification Search
None
See application file for complete search history.

(56) References Cited

U.S. PATENT DOCUMENTS

| | | | | |
|---|---|---|---|---|
| 8,635,012 B2 * | 1/2014 | O'Sullivan | ........ | G01C 21/3469 701/411 |
| 8,744,766 B2 | 6/2014 | Rakshit | | |
| 2008/0024323 A1 * | 1/2008 | Kadaba | .............. | G01N 33/0075 340/905 |
| 2008/0033644 A1 * | 2/2008 | Bannon | .............. | G01C 21/3461 701/414 |
| 2013/0080053 A1 * | 3/2013 | Rakshit | .............. | G01C 21/3461 701/527 |
| 2014/0032704 A1 * | 1/2014 | Painter | ................. | G08B 27/006 709/217 |

(Continued)

FOREIGN PATENT DOCUMENTS

| | | |
|---|---|---|
| CN | 204302267 U | 4/2015 |
| FR | 2 983 948 A1 | 6/2014 |
| WO | WO 2015/175304 A1 | 11/2015 |

OTHER PUBLICATIONS

Brienza S. et al., "A Low-Cost Sensing System for Cooperative Air Quality Monitoring in Urban Areas", Sensors 15:12242-12259 (2015).

(Continued)

*Primary Examiner* — Jelani A Smith
*Assistant Examiner* — Kelly D Williams
(74) *Attorney, Agent, or Firm* — Scully, Scott, Murphy & Presser, P.C.; Joseph Petrokaitis

(57) ABSTRACT

Systems and methods for navigating in consideration of estimated air quality in an individual area of a geographic region includes receiving traffic data for the individual area and sensor data of environmental pollution sensors within the individual region.

20 Claims, 5 Drawing Sheets

(56) References Cited

U.S. PATENT DOCUMENTS

2014/0303885 A1* 10/2014 Kamada ............. G01C 21/3461
                                                            701/400
2017/0091350 A1*  3/2017 Bauer ................. G06F 17/5095
2018/0004211 A1*  1/2018 Grimm ............. G01C 21/3407

OTHER PUBLICATIONS

Devarakonda S. et al., "Real-Time Air Quality Monitoring Through Mobile Sensing in Metropolitan Areas", Proceedings of the 2nd ACM SIGKDD International Workshop on Urban Computing, Article No. 15 (8 pages) (Aug. 11-14, 2013).

Hasenfratz D. et al., "Deriving High-Resolution Urban Air Pollution Maps Using Mobile Sensor Nodes", Pervasive and Mobile Computing 16:268-285 (2015).

Hasenfratz D. et al., "Health-Optimal Routing in Urban Areas", Proceedings of the 14th Conference on Information Processing in Sensor Networks (1 page), Abstract only (Apr. 13-16, 2015).

Mell P., et al., "The NIST Definition of Cloud Computing", NIST Special Publication 800-145, National Institute of Standards and Technology, U.S. Department of Commerce, pp. 1-7 (Sep. 2011).

"Crowdsourcing High-Resolution Air Quality Sensing", https://web.archive.org/web/20150118200813/http://www.transport.epfl.ch/crowdsense., (2 pages) (Jan. 18, 2015).

* cited by examiner

NAVIGATION SYSTEM BASED ON AIR POLLUTION EXPOSURE PROFILING

FIELD

The present application relates generally to computers, and computer applications, and more particularly to computer-implemented methods to provide navigation based on estimated pollution levels.

BACKGROUND

Typical navigation devices and methods take into account the mileage of one or more routes between an embarkation point and a destination. Some navigation devices and methods also are able to take into account existing traffic patterns between the embarkation point and the destination.

Further, typical pollution estimation programs and devices rely on historical data from disparate monitoring sites and/or a limited number of additional sensors.

What is desired is a navigation system, device and method that can weigh navigation elements, such as mileage and/or existing traffic conditions, along with pollution level estimates along a route such that a user can select a route with comparatively low pollution levels.

BRIEF SUMMARY

One embodiment of a computer implemented method for providing navigation based on estimated pollution levels includes the steps of receiving traffic data related to an individual area of a geographic region and sensor data of environmental pollution sensors within the individual area of a geographic region, correlating the traffic data and the received sensor data by time, transmitting correlated data and deleting the correlated data below a predetermined threshold to create filtered data, determining if the filtered data is from one or more of an individual area of usual diffusion of air pollutants and an individual area of atypical diffusion of air pollutants, wherein the individual area is of usual diffusion of air pollutants if the individual area has a reduction in the level of air pollutants below a threshold level over a predetermined time after a traffic level decreases based on a historical data of air pollutant levels, and wherein the individual area is of the atypical diffusion of air pollutants if the individual area has a reduction in the level of air pollutants above a threshold level over a predetermined time after a traffic level decreases based on the historical data of air pollutant levels, transmitting the filtered data from individual areas of usual diffusion and estimating air quality in the individual area by correlating received filtered data to historical pollution data, transmitting filtered data from individual areas of atypical diffusion and estimating a weight to the individual area, estimating air quality in the individual area based on the filtered data and the weight, repeating each of the previous steps for at least one other individual area of the geographic region and selecting a route through the two or more individual areas of the geographic region that have air quality above a predetermined threshold.

A system that includes one or more processors operable to perform one or more methods described herein also may be provided.

A computer readable storage medium storing a program of instructions executable by a machine to perform one or more methods described herein also may be provided.

Further features as well as the structure and operation of various embodiments are described in detail below with reference to the accompanying drawings. In the drawings, like reference numbers indicate identical or functionally similar elements.

DETAILED DESCRIPTION

The disclosure is directed to systems and methods for determining a route from a starting point in a geographic region to a destination in a geographic region that would expose a user of a vehicle to the least air pollutants or a reduced amount of air pollutants.

In some embodiments, to determine the route, the geographic region can be is divided into a number of individual areas of a predetermined size. For example, a city can be divided into 100 meter by 100 meter squares, each of which can be assigned an air quality according to the disclosed method and system. In other examples, different sizes of individual areas can be created, and can include different shapes.

Figure 1:
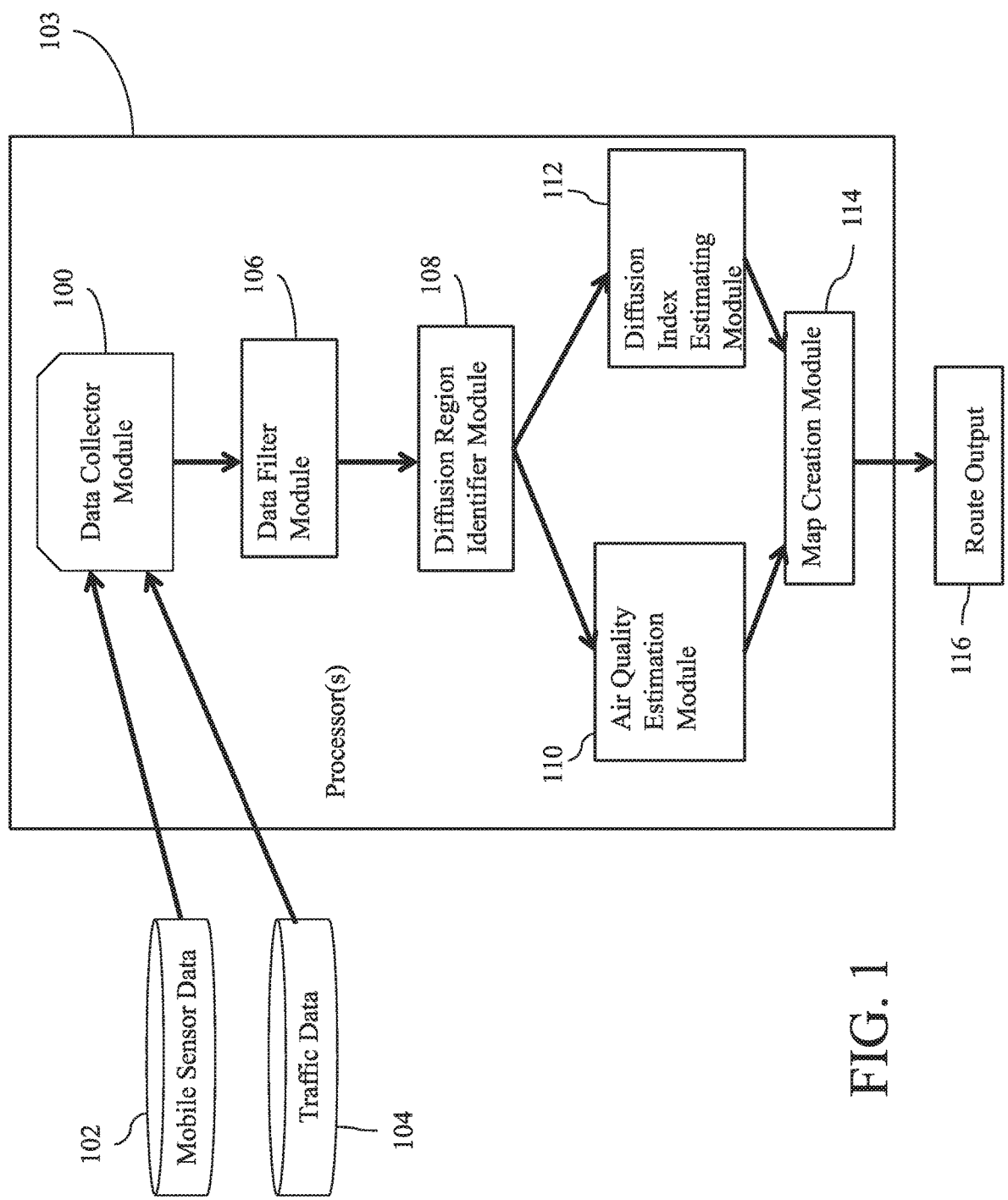
FIG. 1 depicts an overall system environment according to an embodiment of the present invention.
Figure 2:
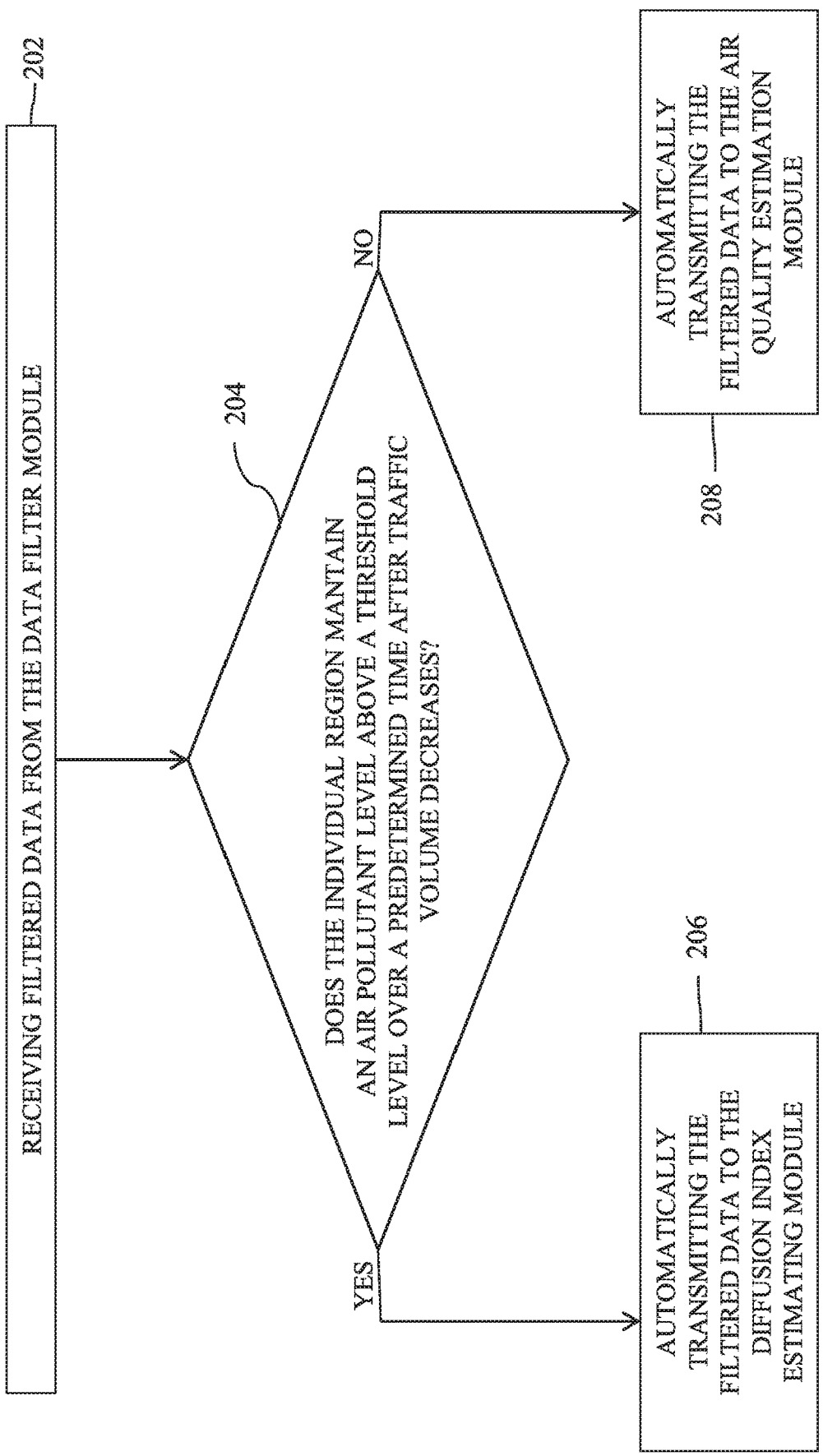
FIG. 2 is a flow diagram illustrating a method of estimating pollution levels according to an embodiment of the present invention.

FIG. 1 depicts an example of a computer system for estimating air pollution exposure. In particular, FIG. 1 illustrates the receipt of mobile sensor data 102 and traffic data 104 by one or more processors 103. Included as part of the one or more processors 103 are a data collector module 100, a data filter module 106, a diffusion region identifier module 108, an air quality estimation module 110, a diffusion index estimating module 112 and a map creation module 114. An exemplary flow diagram of the system is shown in FIG. 2.

To estimate the air quality along routes at the time the user wants to travel from the starting point to the destination, the data collector module 100, as shown in FIG. 1, receives an input of mobile sensor data 102 and traffic data 104. Another possible input received by the data collector module is data from stationary air quality monitoring stations. Input from these stationary air quality monitoring stations can include air pollution levels, wind speed and direction, various weather values such as air pressure, topographical data and distance from the stationary air quality monitoring station to the route.

Traffic data 104 is data for one or more roads in the individual areas. Traffic data for a specific section of road within the individual area is a function of distance of road (d), average speed of the vehicles (s) and average flow rate of vehicles (f) to determine a traffic volume (V): $V=(d/s)*f$. Traffic data can be collected according to a certain regions traffic measurements (such as a cities measured traffic statistics), or by internet sources such as Google™ and Tom- Tom™. Real time and historical traffic data can be gathered and relied upon and used by the data collector module 100.

Although traffic volume V can lead to higher pollutant levels in the individual area, other environmental factors can affect the pollutant levels, such as meteorological conditions and topography. Therefore, to estimate air quality, mobile sensor data 102 is also received by data collector module 100 in some embodiments.

Mobile sensor data 102 is collected by one or more air quality sensors attached to vehicles, such as public buses, travelling along various routes in the geographic area. These mobile sensors are transported along various routes in the geographic area and measure one or more air quality components at predetermined times and/or locations. These air quality components can include any measurable feature of the air, such as particulate matter levels, a portion of volatile organic carbons or total volatile organic carbons (TVOC), carbon monoxide, sulfur oxides, nitrogen oxides, as examples. Other air quality components can also be measured by the mobile sensors.

The mobile sensor data 102, along with the air quality data, provides time of measurement data and also positional data of the sensor at the time of measurement. The data collector module 100 can then substantially correlate the location within the geographic region of the mobile sensor data 102 (based on the time of measurement data and the positional data) with the traffic data 104 in the same or nearly the same location within the geographic area.

Upon correlation, the data collector module 100 has a number of data points for a number of locations within the geographic area, including positional location, time of last air quality component data measurement, levels of one or more pollutants in the last air quality data measurement, and traffic volume V at the time and location of the last air quality data measurement.

Optionally, the data collector 100 can receive and also correlate weather data for the geographic area, or any portion of the geographic area. This weather data can include, for example, wind speeds, temperature, barometric pressure, etc.

The correlated data is transmitted by the data collector module 100 to the data filter module 106. The data filter module 106 transmits the filtered data to the diffusion region identifier module 108. Diffusion region identifier module 108 determines from the received filtered data which of the individual areas in the geographic region have usual diffusion of air pollutants and which individual areas have atypical diffusion of air pollutants.

After diffusion region identifier module 108 receives the filtered data from data filter module 106 in step 202 of FIG. 2, the diffusion region identifier module 108 decides the individual area in the geographic region is to be assigned as having usual diffusion of air pollutants or assigned as having atypical diffusion of air pollutants in step 204.

The diffusion region identifier module 108 assigns individual areas as having atypical diffusion of air pollutants in step 204 if the individual area is estimated to maintain an air pollutant level above a threshold level over a predetermined time after traffic volume V decreases based on historical data. As one example, the threshold level of TVOC in one individual area is initially above 480 parts per million (ppm) and is maintained above 480 ppm for 2 hours after the morning commute time. In this example, the traffic volume V does not closely follow TVOC levels.

If the individual area is estimated as above a threshold level over a predetermined time after traffic volume V decreases in step 204, the diffusion region identifier module 108 automatically transmits filtered data to the diffusion index estimating module 112 in step 206. Diffusion index estimating module 112 also includes a stored amount of historical data of traffic data and air pollutant levels for the individual area.

The diffusion region identifier module 108 assigns individual areas as having usual diffusion of air pollutants in step 204 if the individual area is estimated to have a reduction in the level of air pollutants below a threshold level over a predetermined time after traffic volume V decreases based on historical data. As one example, the threshold level of TVOC in one individual area is initially above 480 ppm but decreases below 480 ppm within 2 hours after the morning commute time.

If the individual area is estimated as below a threshold level over a predetermined time after traffic volume V decreases in step 204, the diffusion region identifier module 108 automatically transmits filtered data to the air quality estimation module 110 in step 208.

Based on historical data of traffic values and previously measured air quality from the mobile sensors, the air quality estimation module 110 estimates what the level of environmental pollution is in the individual area. The air quality estimation module 110 makes this estimation by a multi-variable nonlinear regression model, the variables including traffic volume at the time of the historical data, time of day of the historical data, environmental pollution level at the time of the historical data, and optionally weather at the time of the historical data.

The air quality estimation module 110 then correlates the recently received filtered data of traffic data to the historical data to estimate an air pollution level in the individual area and assigns a confidence level of the correlation. This correlation can be accomplished with an interpolation algorithm, such as, for example, a Kriging algorithm. The confidence assigned to the correlation is provided by the interpolation algorithm, and depends on a distance between the location of the measured data (spatial and temporal) and the individual area.

The air quality estimation module 110 can repeat this process for several of the individual areas based on the traffic data in that individual area.

The air quality estimation module 110 estimates air pollution levels in individual areas previously identified as usual diffusion regions, while the diffusion index estimating module 112 estimates air pollution levels in individual areas previously identified as atypical diffusion regions. These previously identified "atypical" diffusion regions are identified as such because there is previous mobile sensor data that exceeds an estimated range of air pollution levels for given traffic conditions.

For example, an atypical diffusion region can have heavy traffic, but unexpectedly low air pollution levels. In this example, the atypical diffusion region can include a channel for wind to pass through and disperse air pollution. Thus, in some embodiments the diffusion index estimating module 112 can further base its estimate of air pollution levels in such atypical diffusion on previous data.

The estimates from the air quality estimation module 110 and from the diffusion estimating module 112 can be combined in the map creation module 114, which can create a map of at least two different individual areas of the geographic region and their corresponding air quality or air pollution levels. This map can contain pollution estimates and air quality levels for at least two individual areas along at least two routes (through the at least two individual areas) between a starting point in the geographic region and a destination in the geographic region. The map creation module 114 can then determine which of the routes has the least estimated pollution levels or which routes have an air quality above a predetermined threshold level along the length of the route and output that determined route as route output 116. Route output 116 includes navigational instructions from the starting point in the geographic area and the destination in the geographic area.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure that includes a network of interconnected nodes.

Figure 3:
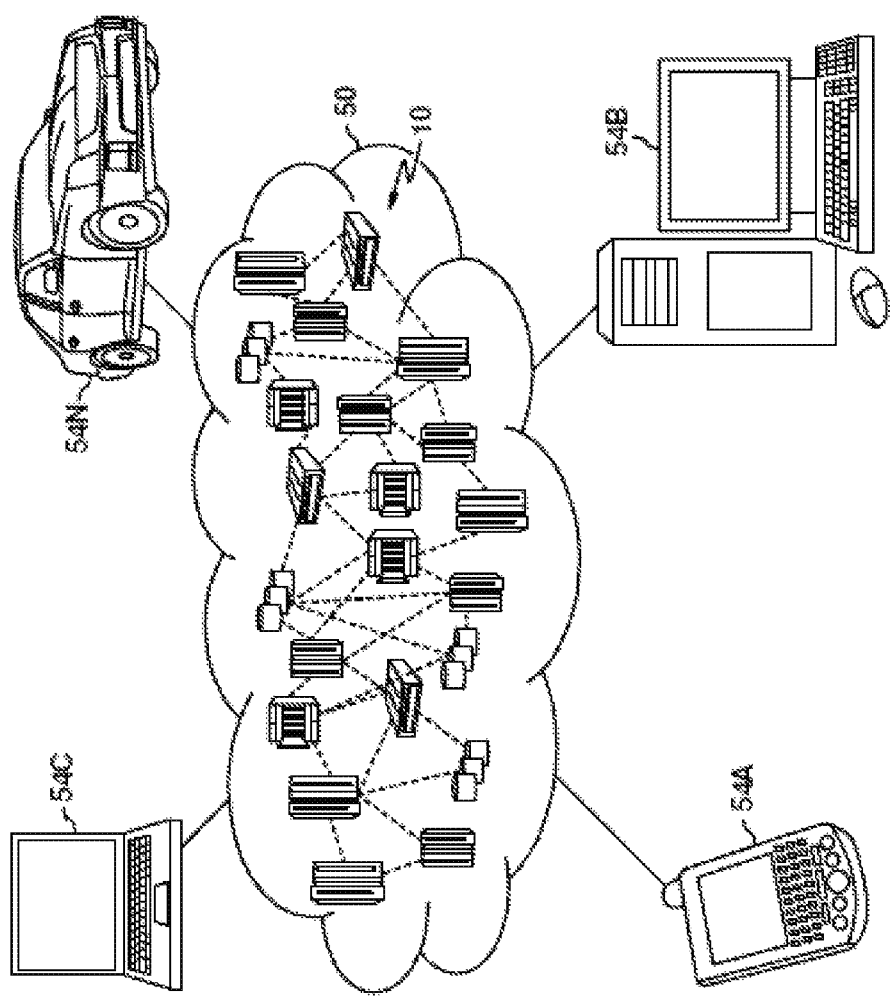
FIG. 3 depicts a cloud computing environment according to an embodiment of the present invention.

Referring now to FIG. 3, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 3 are intended to be illustrative only and that computing nodes 10 and cloud computing environment 50 can communicate with any type of computerized device over any type of network and/or network addressable connection (e.g., using a web browser).

Figure 4:
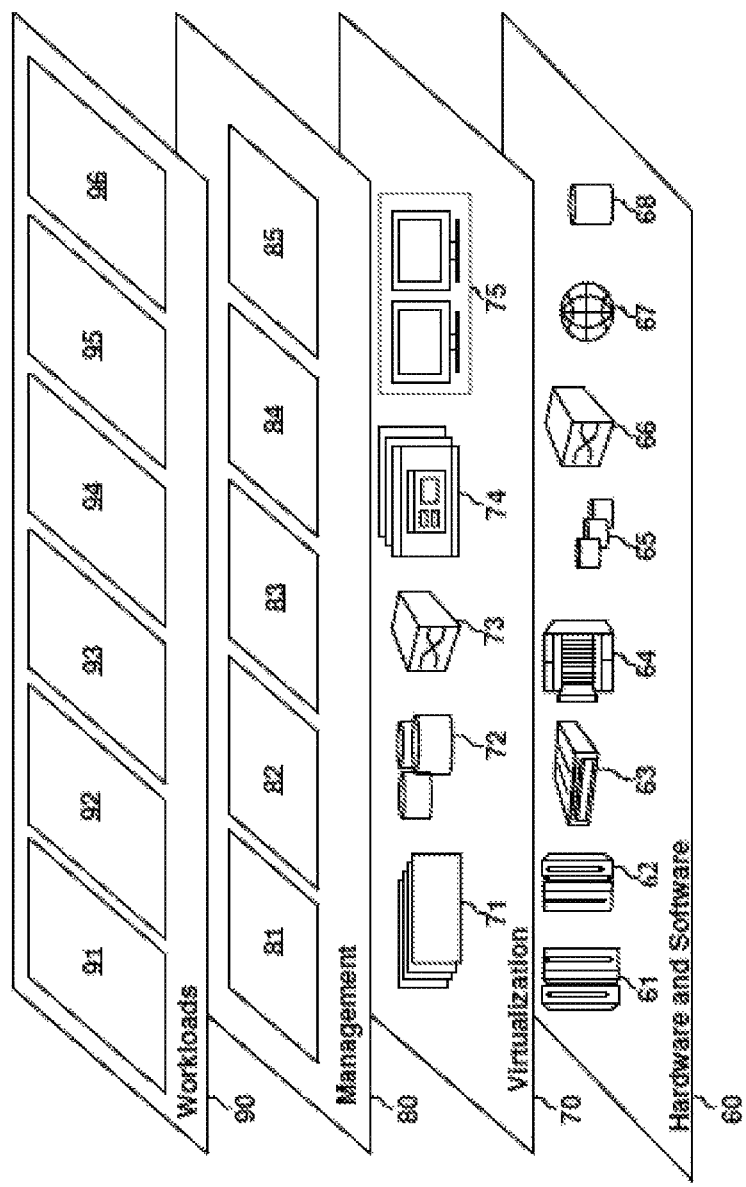
FIG. 4 depicts abstraction model layers according to an embodiment of the present invention.

Referring now to FIG. 4, an exemplary set of functional abstraction layers provided by cloud computing environment 50 (FIG. 3) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and navigation processing in accordance with the present invention 96.

Figure 5:
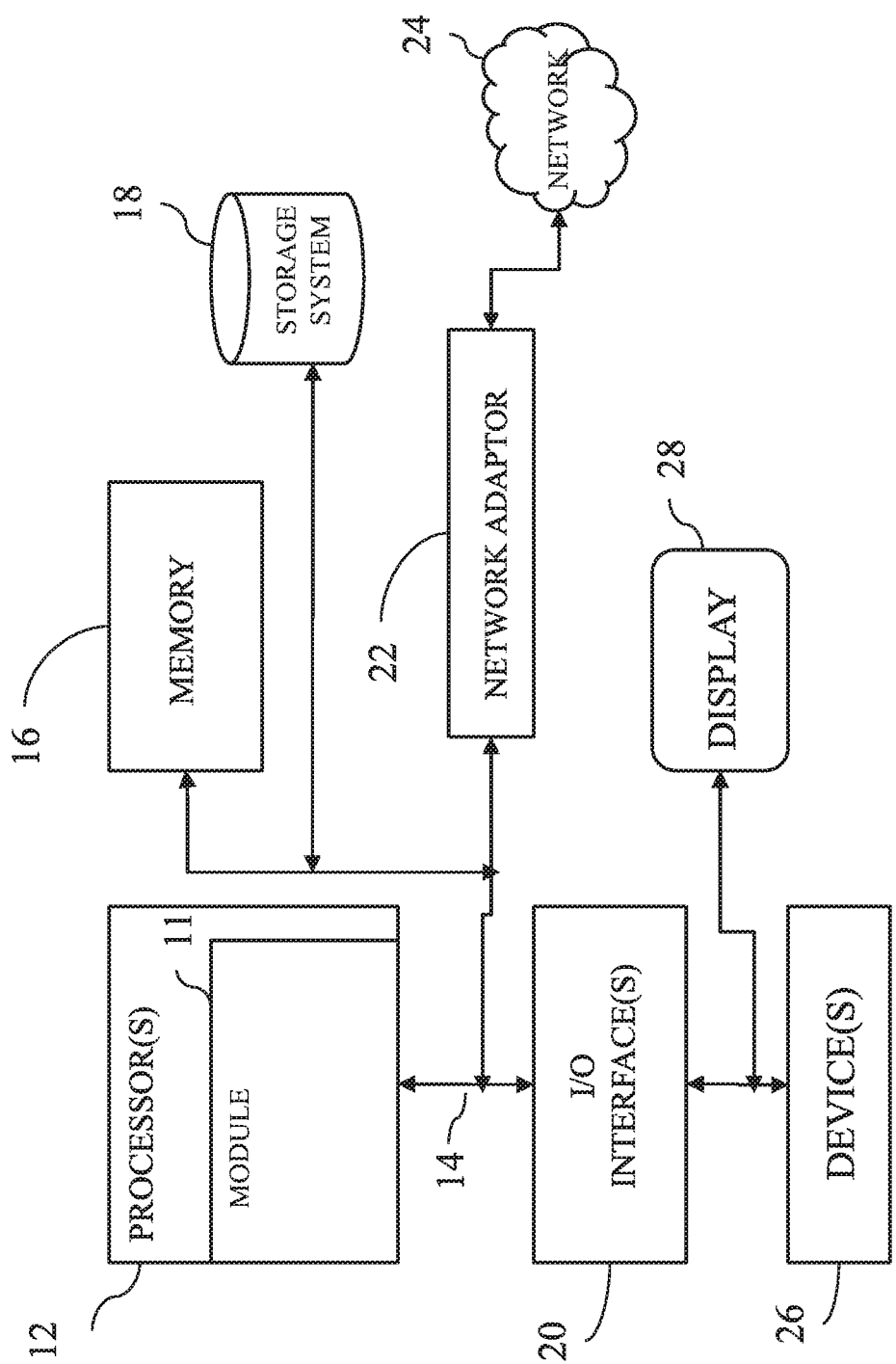
FIG. 5 illustrates a schematic of an example computer or processing system according to an embodiment of the present disclosure.

FIG. 5 illustrates a schematic of an example computer or processing system according to an embodiment of the present disclosure. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 5 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include a module 11 that performs the methods described herein. The module 11 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer implemented method for navigating, comprising:
   receiving traffic data related to an individual area of a geographic region and sensor data of environmental pollution sensors within the individual area of the geographic region;
   correlating the traffic data and the received sensor data by time;
   transmitting the correlated data and deleting the correlated data below a predetermined threshold to create filtered data;
   determining if the filtered data is from one or more of an individual area of usual diffusion of air pollutants and an individual area of atypical diffusion of air pollutants,
   wherein the individual area is of usual diffusion of air pollutants if the individual area has a reduction in the level of air pollutants below a threshold level over a predetermined time after a traffic level decreases based on a historical data of air pollutant levels, and wherein the individual area is of the atypical diffusion of air pollutants if the individual area has a reduction in the level of air pollutants above the threshold level over a predetermined time after a traffic level decreases based on the historical data of air pollutant levels;
   automatically transmitting the filtered data from the individual area of usual diffusion and estimating air quality in the individual area of usual diffusion by correlating the filtered data received to historical pollution data;
   automatically transmitting filtered data from the individual area of atypical diffusion and estimating a weight to the individual area of atypical diffusion;
   estimating air quality in the individual area of the geographic region based on the filtered data transmitted from either the individual area of usual diffusion or the individual area of atypical diffusion, and the weight;
   repeating each of the previous steps for at least one different individual area of the geographic region that is in a different geographic region as compared to the individual area of the geographic region;
   selecting a route through two or more different individual areas of the geographic region that have air quality above a predetermined threshold; and
   outputting the route, the route comprising navigational instructions from a starting point in the geographic region to a destination in the geographic region.

2. The computer implemented method of claim 1, wherein traffic data of the individual area of the geographic region is a traffic volume (V) determined according to the formula $V=(d/s)*f$, wherein d is a distance of road in the individual area of the geographic region, s is the average speed of vehicles in the individual area of the geographic region and f is the average flow rate of vehicles in the individual area of the geographic region.

3. The computer implemented method of claim 1, wherein the environmental pollution sensors gather data on one or more of: particulate matter levels, a portion of volatile organic carbons or total volatile organic carbons (TVOC), carbon monoxide, sulfur oxides, and nitrogen oxides.

4. The computer implemented method of claim 1, wherein the data collector module receives weather data of the individual area and correlates the weather data to the traffic data and the sensor data.

5. The computer implemented method of claim 4, wherein the weather data comprises one or more of wind speed, temperature and barometric pressure.

6. The computer implemented method of claim 1, wherein software is provided as a service in a cloud environment.

7. The computer implemented method of claim 1, wherein selecting a route through the two or more different individual areas of the geographic region enables unilaterally provisioning computing capabilities.

8. A system for providing navigation, comprising:
   one or more computer readable storage devices having executable program instructions embodied therewith;
   one or more processors operably coupled to the one or more computer readable storage devices;
   one or more processors operable to receive traffic data related to at least two individual areas of a geographic region and sensor data of environmental pollution sensors within the at least two individual areas of the geographic region, wherein each of the at least two individual areas of the geographic region are in different geographic locations;
   one or more processors operable to correlate the traffic data and the received sensor data by time;
   one or more processors operable to transmit the correlated data and delete the correlated data below a predetermined threshold to create filtered data;
   one or more processors operable to transmit the filtered data to a diffusion region identifier module, wherein the diffusion region identifier module determines if the filtered data is from an individual area of usual diffusion of air pollutants or from an individual area of atypical diffusion of air pollutants;
   one or more processors operable to determine if the filtered data is from one or more of an individual area of usual diffusion of air pollutants and an individual area of atypical diffusion of air pollutants,
   wherein the individual area is of usual diffusion of air pollutants if the individual area has a reduction in the level of air pollutants below a threshold level over a predetermined time after a traffic level decreases based on a historical data of air pollutant levels, and wherein the individual area is of the atypical diffusion of air pollutants if the individual area has a reduction in the level of air pollutants above a threshold level over a predetermined time after a traffic level decreases based on the historical data of air pollutant levels;

one or more processors operable to automatically transmit the filtered data from individual areas of usual diffusion and estimate air quality in the at least two individual areas by correlating received filtered data to historical pollution data;

one or more processors operable to automatically transmit filtered data from individual areas of atypical diffusion and estimating a weight to the individual area of atypical diffusion;

one or more processors operable to estimate air quality in the at least two individual areas based on the filtered data transmitted from either the individual area of usual diffusion or the individual area of atypical diffusion, and the weight;

one or more processors operable to select a route through the at least two individual areas of the geographic region that have air quality above a predetermined threshold; and one or more processors operable to output the route, the route comprising navigational instructions from a starting point in the geographic region to a destination in the geographic region.

9. The system of claim 8, wherein traffic data of each of the at least two individual areas of the geographic region is a traffic volume (V) determined according to the formula $V=(d/s)*f$, wherein d is a distance of road in the individual areas of the geographic region, s is the average speed of vehicles in the individual areas of the geographic region and f is the average flow rate of vehicles in the individual areas of the geographic region.

10. The system of claim 8, wherein the environmental pollution sensors gather data on one or more of: particulate matter levels, a portion of volatile organic carbons or total volatile organic carbons (TVOC), carbon monoxide, sulfur oxides, and nitrogen oxides.

11. The system of claim 8, wherein the data collector module receives weather data of each individual area and correlates the weather data to the traffic data and the sensor data.

12. The system of claim 11, wherein the weather data comprises one or more of wind speed, temperature and barometric pressure.

13. The system of claim 8, wherein software is provided as a service in a cloud environment.

14. The system of claim 8, wherein selecting a route through the two or more individual areas of the geographic region enables unilaterally provisioning computing capabilities.

15. A computer readable storage medium storing a program of instructions executable by a machine to perform a method of navigation, the method comprising:

Receiving, by a computer, traffic data related to an individual area of a geographic region and sensor data of environmental pollution sensors within the individual area of a geographic region, a processor of the computer having program instructions and configured to perform the steps of:

correlating the traffic data and the received sensor data by time;

transmitting the correlated data and deleting the correlated data below a predetermined threshold to create filtered data;

determining if the filtered data is from one or more of an individual area of usual diffusion of air pollutants and an individual area of atypical diffusion of air pollutants, wherein the individual area is of usual diffusion of air pollutants if the individual area has a reduction in the level of air pollutants below a threshold level over a predetermined time after a traffic level decreases based on a historical data of air pollutant levels, and wherein the individual area is of the atypical diffusion of air pollutants if the individual area has a reduction in the level of air pollutants above a threshold level over a predetermined time after a traffic level decreases based on the historical data of air pollutant levels;

automatically transmitting the filtered data from the individual area of usual diffusion and estimating air quality in the individual area by correlating received filtered data to historical pollution data;

automatically transmitting filtered data from the individual area of atypical diffusion and estimating a weight to the individual area of atypical diffusion;

estimating air quality in the individual area of the geographic region based on the filtered data transmitted from either the individual area of usual diffusion or the individual area of atypical diffusion, and the weight;

repeating each of the previous steps for at least one different individual area of the geographic region that is in a different geographic region as compared to the individual area of the geographic region;

selecting a route through two or more different individual areas of the geographic region that have air quality above a predetermined threshold; and outputting the route, the route comprising navigational instructions from a starting point in the geographic region to a destination in the geographic region.

16. The computer readable storage medium of claim 15, wherein traffic data of the individual area of the geographic region is a traffic volume (V) determined according to the formula $V=(d/s)*f$, wherein d is a distance of road in the individual area of the geographic region, s is the average speed of vehicles in the individual area of the geographic region and f is the average flow rate of vehicles in the individual area of the geographic region.

17. The computer readable storage medium of claim 15, wherein the environmental pollution sensors gather data on one or more of: particulate matter levels, a portion of volatile organic carbons or total volatile organic carbons (TVOC), carbon monoxide, sulfur oxides, and nitrogen oxides.

18. The computer readable storage medium of claim 15, wherein a data collector module receives weather data of the individual area and correlates the weather data to the traffic data and the sensor data.

19. The computer readable storage medium of claim 18, wherein the weather data comprises one or more of wind speed, temperature and barometric pressure.

20. The computer readable storage medium of claim 15, wherein selecting a route through the two or more individual areas of the geographic region enables unilaterally provisioning computing capabilities.

* * * * *